United States Patent [19]
Gilchrist et al.

[11] Patent Number: 5,916,747
[45] Date of Patent: Jun. 29, 1999

[54] METHOD AND APPARATUS FOR ALIGNMENT OF SIGNALS FOR USE IN DNA BASED-CALLING

[75] Inventors: Rodney D. Gilchrist, Oakville; Vrijmoed Chi, Mississauga, both of Canada

[73] Assignee: Visible Genetics Inc., Toronto, Canada

[21] Appl. No.: 08/670,534

[22] Filed: Jun. 27, 1996

Related U.S. Application Data

[63] Continuation-in-part of application No. 08/497,202, Jun. 30, 1995.

[51] Int. Cl.$^6$ ............................................. C12Q 1/68
[52] U.S. Cl. ........................... 435/6; 435/91.1; 435/287.1; 364/148.07
[58] Field of Search .......................... 435/6, 91.1, 287.2, 435/287.1; 536/23.1, 25.3; 935/76, 77; 472/50, 67, 68.1; 364/148.07, 178, 400

[56] References Cited

U.S. PATENT DOCUMENTS

| | | | |
|---|---|---|---|
| 3,742,202 | 6/1973 | Spreitzhofer | 235/183 |
| 4,329,591 | 5/1982 | Fujiwara et al. | 250/548 |
| 4,811,218 | 3/1989 | Hunkapiller et al. | 364/413.01 |
| 4,823,007 | 4/1989 | Hanson | 250/327.2 |
| 5,119,316 | 6/1992 | Dam et al. | 364/498 |
| 5,273,632 | 12/1993 | Stockham et al. | 204/180.1 |
| 5,290,419 | 3/1994 | Kambara et al. | 204/299 R |
| 5,360,523 | 11/1994 | Middendorf et al. | 204/182.8 |
| 5,365,455 | 11/1994 | Tibbetts et al. | 364/497 |
| 5,419,825 | 5/1995 | Fujii | 204/299 R |
| 5,502,773 | 3/1996 | Tibbetts et al. | 382/129 |

FOREIGN PATENT DOCUMENTS

| | | |
|---|---|---|
| 0198403 | 10/1986 | European Pat. Off. . |
| 0476712 | 3/1992 | European Pat. Off. . |
| 0592060 | 4/1994 | European Pat. Off. . |
| 2225139 | 5/1990 | United Kingdom . |

OTHER PUBLICATIONS

Bowling et al., "Neighboring nucleotide interactions during DNA sequencing gel electrophoresis" *Nucl. Acids. Res.* 19: 3089–3097 (1991).

Giddings et al., "An adaptive, object oriented strategy for base calling in DNA sequence analysis" *Nucl. Acids, Res.* 21: 4530–4540 (1993).

Golden III, et al., "Pattern Recognition for Automated DNA Sequencing: I. On–Line Signal Conditioning and Feature Extraction for Base calling".

Ingber and Rosen, "Genetic Algorithms and Very Fast Simulated Annealing: A Comparison" *Mathematical and Computer Modelling* 16: 87–100 (1992).

Ingber, L., "Simulated Annealing: Practice versus Theory", *Mathematical and Computer Modelling* 18: 29–57 (1993).

Ingber,L., "Adaptive Simulated Annealing (ASA): Lessons Learned". *Control and Cybernetics* 1995).

Ingber, L., "Very Fast Simulated Re–Annealing" *Mathematical and Computer Modelling* 12: 967–973 (1989)— Draft of Paper.

Landegren et al., "DNA Diagnostics—Molecular Techqniues and Automation" *Science* 242: 229–237 (1988).

Mayrand et al., "The use of fluorescence detection and internal lane standards to size PCR products".

Tibbetts et al., "Neural Networks for Automated Basecalling of gel–Based Sequencing Ladders".

"Lester Ingber's Code and Reprint Archive," http://www.ingber.com, pp. 1–16, May 1, 1997.

*Primary Examiner*—Scott W. Houtteman
*Attorney, Agent, or Firm*—Oppedahl & Larson LLP

[57] ABSTRACT

Data traces from four channels of an automated electrophoresis detection apparatus are aligned by identifying peaks in each of the four data traces; normalizing the heights of the peaks in each of the data traces to a common value to generate four normalized data traces; combining the four normalized data traces in an initial alignment; and determining coefficients of shift and stretch for selected data points within each normalized data trace. The coefficients are determined by optimizing a cost function which reflects the extent of overlap of peaks in the combined normalized data traces to which the coefficients have been applied. The cost function is optimized when the extent of overlap is at a minimum. The coefficients are then used to generate a warp function for each normalized data trace. These warp function are applied to their respective data traces to produce four warped data traces which are aligned to form an aligned data set. The aligned data set may be displayed on a video screen of a sequencing apparatus, or may be used as the data set for a base-calling process.

27 Claims, 5 Drawing Sheets

METHOD AND APPARATUS FOR ALIGNMENT OF SIGNALS FOR USE IN DNA BASED-CALLING

This application is a continuation-in-part of copending U.S. patent application Ser. No. 08/497,202, filed Jun. 30, 1995, which is incorporated herein by reference.

BACKGROUND TO THE INVENTION

This invention relates to a method of processing output signals from an automated electrophoresis detection apparatus, and to an apparatus which employs this method for sequencing nucleic acids.

One of the steps in nucleotide sequence determination of a subject nucleic acid molecule is interpretation of the pattern of nucleic acid fragments which results from electrophoretic separation of fragments, or reaction products, of a DNA sequencing reaction (the "fragment pattern"). The interpretation, colloquially known as "base calling", involves determination from the recorded fragment pattern of the order of four nucleotide bases, A (adenine), C (cytosine), G (guanine) and T (thymine) for DNA or U (uracil) for RNA in the subject nucleic acid molecule.

The chemistry employed for a DNA sequencing reaction using the dideoxy (or chain-termination) sequencing technique is well known, and was first reported by Sanger et al. (Proc. Natl. Acad. Sci. USA 74: 5463–5467 (1977)). Four samples of nucleic acid fragments (terminating in A, C, C, or T(U) respectively in the Sanger et al. method) are loaded at a loading site at one end of an electrophoresis gel. An electric field is applied across the gel, and causing the fragments to migrate from the loading site towards the opposite end of the gel. During this electrophoresis, the gel acts as a separation matrix. The fragments, which in each sample are of an extended series of discrete sizes, separate into bands of discrete species in a lane along the length of the gel. Shorter fragments generally move more quickly than larger fragments.

If the DNA fragments are labeled with a fluorescent label, an automated electrophoresis detection apparatus (also called a "DNA sequencer") can be used to detect the passage of migrating bands in real time. Existing automated DNA sequencers are available from Applied Biosystems, Inc. (Foster City, Calif.), Pharmacia Biotech, Inc. (Piscataway, N.J.), Li-Cor, Inc. (Lincoln, Neb.), Molecular Dynamics, Inc. (Sunnyvale, Calif.) and Visible Genetics Inc. (Toronto). Other methods of detection, based on detection of features inherent to the subject molecule, such as detection of light polarization as disclosed in U.S. patent application Ser. No. 08/387,272, now U.S. Pat. No. 5,543,018, which is incorporated herein by reference, are also possible.

A significant problem in determining a DNA sequence, encountered particularly with high speed DNA sequencing and in sequencing apparatus which do not combine the four sets of sequencing reaction products in a single lane, is alignment of data signals from the four different output channels of an automated DNA sequencing apparatus. Once data is aligned properly, it is relatively straight-forward to base-call it. However, this initial step can be very challenging since the output signal may be erratically shifted and/or stretched as a result of chemistry and gel anomalies. A reliable method of aligning data, that can produce data which takes into account non-linear shifting and stretching of signal output, is highly desirable particularly for high-speed DNA sequencing.

Existing prior art determinants in this field are very limited. Existing automated sequencers traditionally operate at voltages low enough that non-linear shifting is avoided. The use of low voltages, however, limits the speed with which separation of sequencing fragments into discrete bands can be accomplished.

Published methods of computer assisted base calling include the methods disclosed by Tibbetts and Bowling (U.S. Pat. No. 5,365,455) and Dam et al (U.S. Pat. No. 5,119,316) which patents are incorporated herein by reference. Both patents assume alignment of output signals and address only aspects of base-calling from the aligned signals.

It is an object of the present invention to provide a method of aligning real-time signals from the output channels of an automated electrophoresis apparatus.

It is a further object of the invention to provide an improved method of base-calling an DNA signal sequence aligned according to the invention.

It is still a further object of the invention to provide an apparatus for sequencing nucleic acids which utilizes the improved method in accordance with the invention for aligning real-time signals from the output channels of an automated electrophoresis apparatus.

SUMMARY OF THE INVENTION

These and other objects of the invention are achieved using a method for aligning data traces from four channels of an automated electrophoresis detection apparatus, each channel detecting the products of one of four chain-termination DNA sequencing reactions, whereby said four channels together provide information concerning the sequence of all four bases within a nucleic acid polymer being analyzed, comprising the steps of:

(a) identifying peaks in each of the four data traces;

(b) normalizing the height of said peaks in each of said data traces to a common value to generate four normalized data traces;

(c) combining the four normalized data traces in an initial alignment;

(d) determining coefficients of shift and stretch for selected data points within each normalized data trace, said coefficients optimizing a cost function which reflects the extent of overlap of peaks in the combined normalized data traces to which the coefficients have been applied, said cost function being optimized when the extent of overlap is at a minimum;

(e) generating warp functions for the normalized data traces from the coefficients of shift and stretch determined for fsthe selected data points;

(f) applying the warp functions to the respective data trace or normalized data trace to produce four warped data traces; and (g) assembling the four warped data traces to form an aligned data set.

The aligned data set may be displayed on a video screen of a sequencing apparatus, or may be used as the data set for a base-calling process.

DETAILED DESCRIPTION OF THE INVENTION

One aspect of the instant invention is a method of aligning data traces from an automated electrophoresis detection apparatus for use in base-calling. In accordance with the invention, a simulated annealing algorithm is used to determine coefficients of stretch and shift to align data traces, each representing one of the four chain-termination DNA sequencing reactions. With high quality data trace alignment, base-calling may proceed with a high degree of accuracy and repeatability.

"Data trace" as used in the specification and claims of this application refers to the series of peaks and valleys representing the migrating bands of oligonucleotide fragments produced in one chain termination sequencing reaction and detected in a DNA sequencer. The data trace may be either a raw data trace or a "conditioned" data trace.

"Shift" as used in the specification and claims of this application is interchangeable with "offset" and refers to the number of data points which the signal output is displaced, either positively or negatively from its original position.

"Stretch" as used in the specification and claims of this application refers to increase or decrease in spacing between data points of a signal output relative to the original spacing.

A "warp function" as used in the specification and claims of this application is an instantaneous representation of optimized shift and stretch at each data point. The warp function can be represented graphically either as a data point-for-data point plot for one data trace versus a standard or second data trace, or as a plot of displacement as a function of data point number. Standard traces may be a trace representing an average of multiple experimental runs, a base separation function, or a standard derived from a text sequence.

Figure 1:
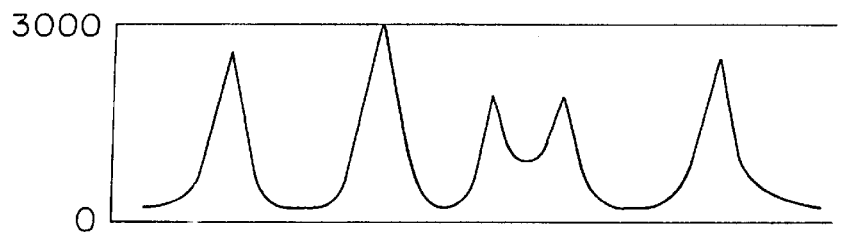
FIG. 1 illustrates a preliminary (unaligned) signal recorded from an automated DNA sequencing apparatus over 15 seconds.

FIG. 1 illustrates a typical raw data trace for one of the four chain-termination DNA sequencing reactions, as detected on a Visible Genetics Inc. MicroGene Blaster™. The X-axis represents time while the Y axis represents fluorescence detection. The data trace reveals a series of bands of fluorescent molecules passing through the detection site, as expected from a typical chain-termination DNA sequencing reaction.

FIG. 1 shows several of the features which complicate the use of raw data for base-calling, and illustrates the need for the present invention to provide appropriately aligned signals for this purpose. In particular, as reflected in FIG. 1, the fluorescence intensity can vary from one band to another. In addition, not all bands are fully resolved, and the spacing between adjacent bands is not always an integral multiple of the theoretical spacing between adjacent bands. The present invention provides a method for converting this raw signal, and its three counterpart signals for the other three sequencing reactions, into aligned data which is highly suitable for base-calling.

The data trace which is processed in accordance with the method of the invention is preferably a signal collected using the fluorescence detection apparatus of an automated DNA sequencer. However, the present invention is applicable to any data set which reflects the separation of oligonucleotide fragments in space or time, including real-time fragment patterns using any type of detector, for example a polarization detector as described in U.S. patent application Ser. No. 08/387,272, now U.S. Pat. No. 5,543,018; densitometer traces of autoradiographs or stained gels; traces from laser-scanned gels containing fluorescently-tagged oligonucleotides; and fragment patterns from samples separated by mass spectrometry.

In the method of the invention, four data traces, one for each sequencing reaction, are normalized using the procedure described below. The normalized data traces are then used to determine a series of stretch and shift coefficients, which are then applied to the normalized data traces to arrive at aligned data traces.

Prior to normalizing and aligning the data traces for the four sequencing reactions using the method of the invention, however, it may be advantageous to condition the signal, although this step is not required. This conditioning can be done, for example, using conventional baseline correction and noise reduction techniques to yield a "conditioned" data trace. As is known in the art, three methods of signal processing commonly used are background subtraction, low frequency filtration and high frequency filtration, and any of these may be used, singly or in combination to produce a conditioned signal to be used as a conditioned data trace in the method of the invention.

Preferably, the data is conditioned by background subtraction using a non-linear filter such as an erosion filter, with or without a low-pass filter to eliminate systemic noise. The preferred low-pass filtration technique is non-causal gaussian convolution.

After any needed conditioning of the data trace is performed, the data trace is normalized to generate a "normalized data trace" which is used to determine coefficients of stretch and shift for base-calling. The normalization process includes the following steps.

Figure 2:
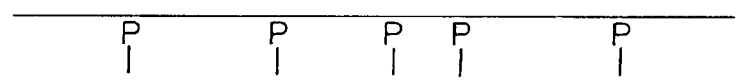
FIG. 2 illustrates the detection of peaks from a preliminary signal.

Firstly, the data trace (raw or conditioned) is searched for peaks. Peaks can be identified as the middle data point of three consecutive data points wherein the inside data point is higher than the two outside data points. FIG. 2. More sophisticated methods of peak detection are also possible. For example, a preferred method involves using the "three-point" method to segment the data trace, and then joining the segments. A trace feature is assigned as an actual peak whenever the difference between a maximum and an adjacent minimum exceeds a threshold value, e.g., 5%. A minimum peak height from the baseline may also be required to eliminate spurious peaks.

An exception is made for the so-called "primer peak" and "termination peak" which are found in some variations of the chain-termination sequencing method. These peaks comprise a large volume of unreacted primer, which tends to interfere with base-calling around the shorter chain-extension products, and a large volume of the complete sequence which may interfere with base-calling around the longest chain-extension products. These peaks are identified and eliminated from consideration either on the basis of their size, their location relative to the start and end of the electrophoresis process, or some other method.

Figure 3:
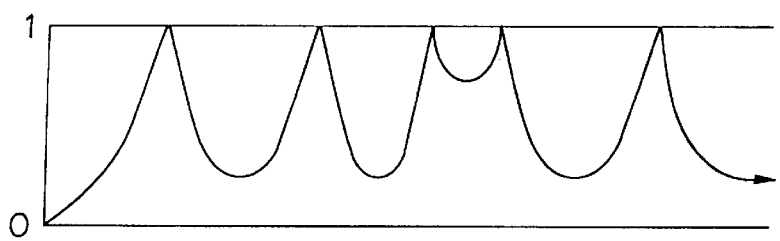
FIG. 3 illustrates a normalized data stream.
Figure 4A:
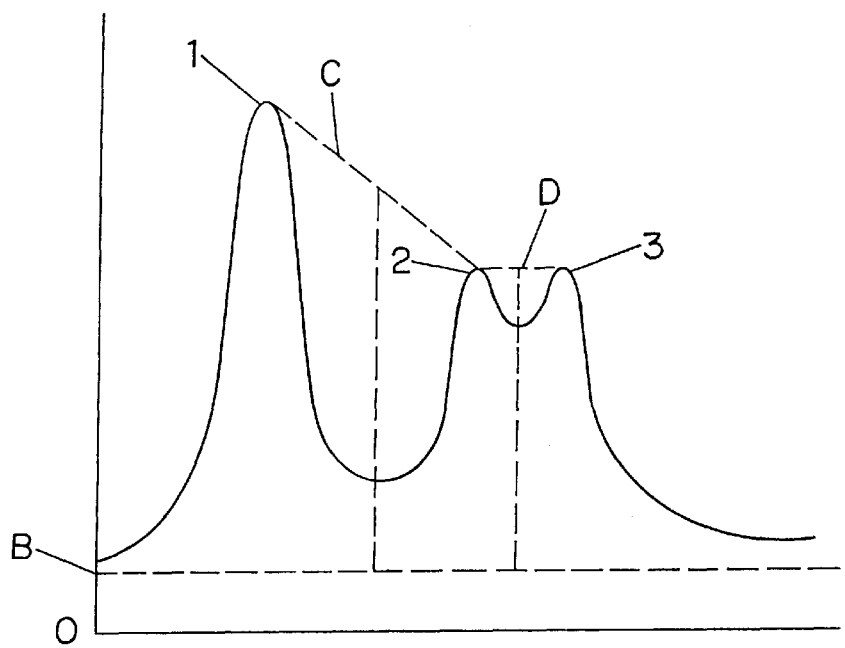
FIGS. 4A and 4B illustrate a normalization method employed for peaks and valleys.
Figure 4B:
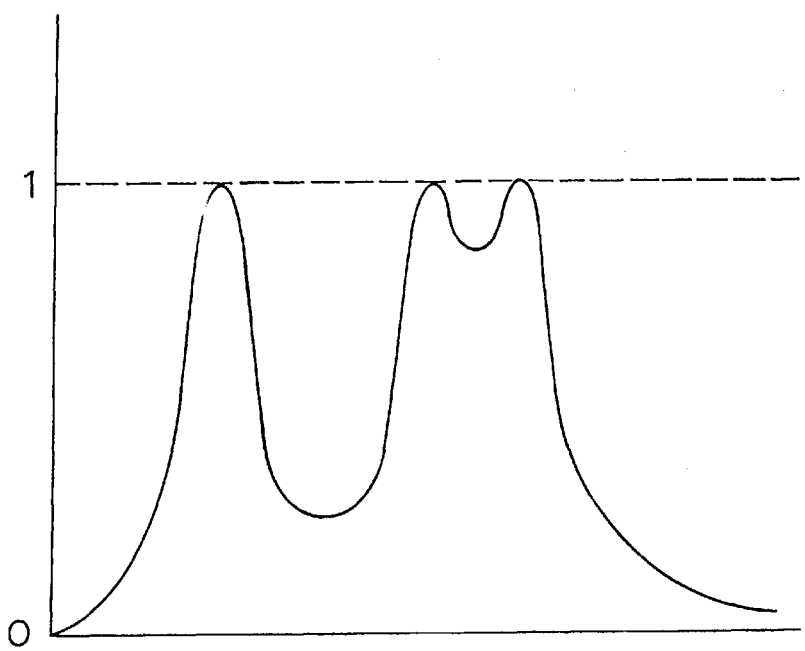

After elimination of the primer and termination peaks, the data trace is normalized so that all of the identified peaks have the same height which is assigned a common value, e.g., 1. (FIG. 3). This process reduces signal variations due to chemistry and enzyme function, and works effectively for homozygous samples and for many heterozygotes having moderate, i.e., less than about 5 to 10%, heterozygosity in a 200 base pair or larger region being sequenced. To normalize the data trace, the points between each peak are assigned a numerical height value based on their position in the data trace relative to a hypothetical line joining consecutive peaks and the base line of the signal. Thus, as shown in FIG. 4A, the valley between peaks 1 and 2 has a minimum at a point which is approximately 25% of the distance from the baseline B to the line C joining peaks 1 and 2. The minimum of this valley is therefore assigned a value of about 0.25. (See FIG. 4B). Similarly, the valley between peaks 2 and 3 has a minimum at a point which is approximately 80% of the distance from the baseline B to the line D joining peaks 2 and 3. The minimum of this valley is therefore assigned a value of about 0.8 in the normalized data trace.

Figure 5A:
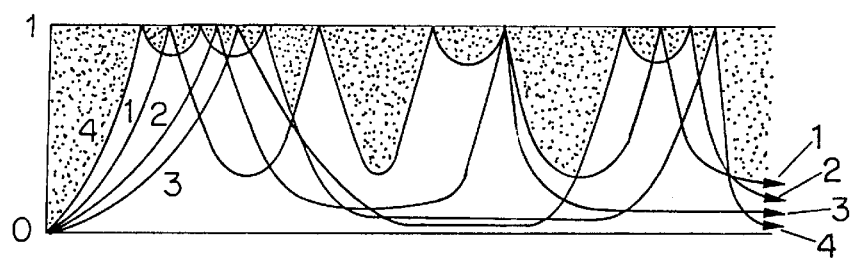
FIGS. 5A and 5B illustrate the preliminary alignment of four normalized data streams representing time based alignment of each of the A, C, G and T output channels.

The next step in the method of the invention is the determination of shift and stretch coefficients for a set of four normalized data traces, one for each sequencing reaction. This is accomplished by combining the four normalized data traces as shown diagrammatically in FIGS. 5A and 5B, and determining coefficients of shift and stretch for selected data points within each normalized data trace which optimize a "cost" function. The cost function generally reflects the extent of overlap of peaks in the combined normalized data traces to which the coefficients have been applied, and is considered optimized when the extent of overlap is at a minimum. It will be understood that the terms "optimized" and "minimum" as used herein do not require absolute optimization to an absolute minimum, which could require unreasonably long periods of analysis time, but only require a practical level of optimization sufficient to achieve satisfactory alignment of the data traces for base-calling.

Figure 5B:
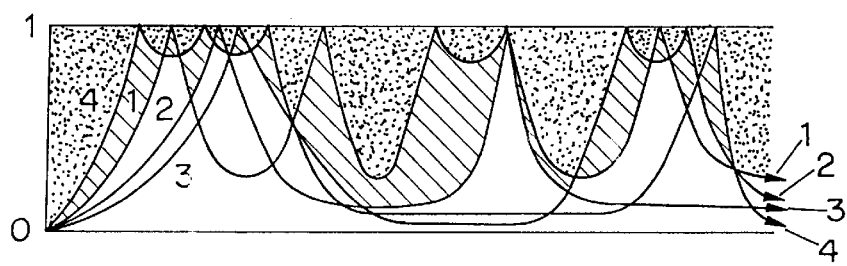

In one embodiment, the cost function measures the total area above the combined normalized data traces, i.e., the dotted area in FIG. 5B. The normalized data traces are then shifted and stretched in an effort to minimize the value of "cost." In a second embodiment, "cost" is set equal to the area below the combined normalized data traces, and the data traces are then shifted and stretched to maximize the value of cost (i.e. reducing the overlap of the peaks). However, it has been found empirically that this latter approach emphasizes less valuable features of the data traces than using the area above the curves as the cost function.

Figure 6:
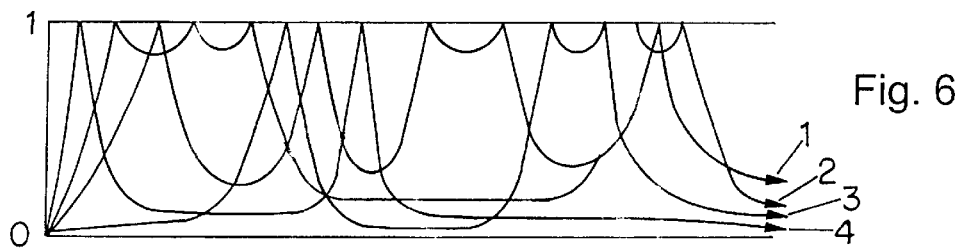
FIG. 6 illustrates alignment of the 4 normalized data streams with respect to minimization of the "cost" function.

In a preferred embodiments, the cost function combines the total area above the combined data traces (the dotted regions in FIG. 5B) with the area below the highest edge formed by the combined data traces and above the second highest edge of the combined data traces (the lined regions in FIG. 5B). The cost function is at a minimum when the first of these areas is minimized and the second of these areas is maximized. When the coefficients which produce the minimum cost are applied to the normalized data traces, an aligned normalized data set as shown in FIG. 6 results.

A preferred method for determining the coefficients of stretch and shift that yield the optimum value of "cost" employs "simulated annealing", although other processes which employ random or directed sparse sampling of the parameters base may also be used. Simulated annealing is a mathematical method of searching a broad parameter space for the "best fit" result, without having to test every member of the parameter space. This method is particularly relevant to signal alignment problems in high speed DNA sequencers because the parameter space for possible coefficient of stretch and shift needs to be extremely broad to accommodate the unpredictability and variation within each electrophoresis run.

The preferred manner of performing a simulated annealing calculation employs a computer. Many computer algorithms employing simulated annealing are known and available to those skilled in the art. Of particular interest are papers by Ingber et al.:

Ingber, A. L., "Very fast simulated re-annealing," *J Mathl. Comput. Modelling* 12(8): 967–973 (1989);

Ingber, A. L. et al., "Genetic algorithms and very fast simulated reannealing: A comparison," *J Mathl. Comput. Modelling* 16 (11): 87–100 (1992);

Ingber, A. L., "Simulated annealing: Practice versus theory," *J Mathl. Comput. Modelling* 18(11): 29–57 (1993); and Ingber, A. L., "Adaptive simulated annealing (ASA): Lessons learned," *J Control and Cybernetics* 25(1): 33–54 (1996)

Each of these papers is incorporated herein by reference.

As employed in the present invention, simulated annealing determines coefficients of stretch and shift for signal outputs from a Visible Genetics MicroGene Blaster™ as follows. Consider a window of normalized signal output. The normalized data trace consists of a series of data points generated every 0.5 seconds. Each peak consists of about 6 to 7 data points, and requires 3 to 3.5 seconds to pass through the detection zone. For convenience of illustration, the window shown represents about 90 data points or about 15 peaks. In a preferred embodiment, however, windows of 180 to 350 data points, representing about 30 to 50 peaks, most preferably of about 250 data points representing about 40 peaks are used.

One window is created for data from each of the four data traces, and the windows would be initially aligned on the basis of data-point number. Superimposing the four windows reveals a non-minimized "cost" result, that is, the amount of "cost" area is greater than it could be.

It is found that a first order equation can be applied to each point of a data trace within the window to modify its position and change the cost area:

$$Y=mX+b$$

where Y=the new position of point X, b=offset (or shift), and m=stretch. A second order or higher equation (with coefficients in addition to stretch and shift being determined) is apparently not necessary to obtain satisfactory results, although second or higher order equations may be used for more sophisticated analyses.

The parameter space for b and m is empirically selected. The offset coefficient (b) usually falls within 30 data points of the initial time-based alignment. Offset steps of 0.35 data points are suitably employed, thus providing a parameter space of 200 choices. For MicroGene Blaster™ data, this offset represents about 5 data peaks. The stretch coefficient (m) usually falls within 5%. These steps are suitably made in 0.66% amounts, thus requiring 15 steps to cover the whole range. The total range of parameters for stretch and shift for each signal output is therefore 3000 (200*15). The range of parameters for alignment of three channels with respect to the fourth channel is therefore 27 billion ($3000^3$).

For each combination of the six parameters tested, the coefficient are applied to the three signal output functions and the functions are stretched and/or shifted accordingly. The adjusted functions are superimposed with the fourth signal output and the "cost" area is re-calculated. The cost will either be lower, higher or the same as before.

Efficient selection of the six parameters is crucial for the discovery of the parameters which provide the lowest cost. The simulated annealing theory selects parameters for testing according to a variation of the Monte Carlo search technique "Boltzmann Annealing" known as Adaptive Simulated Annealing (or Very Fast Simulated Re-Annealing). Simulated Annealing code is generally available to those skilled in the art over the Internet at http://www.ingber.com. The code provides operational steps for rapidly searching a large parameter space for an optimal solution given a cost function. An explanation of Simulated Annealing is found in Ingber, A. L. "Very Fast Simulated Re-Annealing" J. Math. Comput. Modeling (1989) 12: 967–973.

The simulated annealing technique employed in the invention uses algorithms which are well-known to those skilled in the mathematical arts in the following novel fashion. Coefficients of stretch and shift are at first randomly selected and applied to the normalized data traces. The cost is calculated. New coefficients are then selected within a range defined by the annealing schedule (or temperature function "T") which governs the amount by which coefficients may be changed with each trial. The new coefficients are applied and cost is again determined. If the value of cost is lower than before, then the new point is used as the starting point for the next calculation. If the value of cost is higher, then the original coefficients are usually used again as the starting point of the next calculation. As in all simulated annealing processes, however, there is a finite probability P (initially on the order of about 20% or less) that the higher cost value will be used as the starting point. As the number of calculated values increase, T and P are reduced, thus tending to localize the search space around an area of low cost. Annealing temperature schedules allow the "temperature" parameter to be raised to a higher value again at intervals during the search, emulating the process of annealing used to heat treat metals. Eventually, when the search is fully completed, simulated annealing theory argues that the lowest cost value parameters will be found. In the above method, approximately 5000 sets of parameters are tested per calculation, representing 0.00001% of the available parameter field In practice, the "fast annealing" modification of Ingber is found to be satisfactory to obtain cost values low enough to base-call data from the Visible Genetics MicroGene Blaster™ (see Ingber, A. L. "Very Fast Simulated Re-Annealing" J. Mathl. Comput Modeling (1989) 12:967–973).

After the successful determination of the best fit parameter set for a given window of data points, the next window of data is analyzed. The next window is selected to be the same number of data points as the first window, with an overlap of about 50% with the first window. Again, the coefficients of shift and stretch are identified which provide the lowest cost value when applied to the signal output functions. Thus, coefficients are determined for a series of piecewise domains, e.g., piecewise linear or cubic domains. The process of selecting windows and calculating coefficients continues until all the data has been analyzed.

When calculating the coefficients of stretch and shift for windows after the first window, it is sometimes advantageous to use the coefficients from a neighboring window as the starting point for the simulated annealing process since the coefficients for neighboring windows tend to be related. In such cases, the annealing schedule T can be much shorter, for example testing only 1500 sets of coefficients as opposed to 5000. In addition, because it is desirable that the warp functions generated be continuous, subsequent windows may in fact be evaluated as two "sub-windows." In the first sub-window, stretch coefficients are constrained such that the warp function does not change the offset already established at the center of the previous full window. In the second sub-window, the stretch is allowed to vary in a narrow range.

Ultimately, by this process of sliding a window in overlapping steps across the combined normalized data, a "warp function" is arrived at for each normalized data trace. This function reflects the relationship between optimum-cost shift values for each window. By connecting the determined points of the function, a curve is defined which gives coefficients of shift for each point in a data trace, and reflects stretch at each location by the slope of the curve.

Figure 7A:
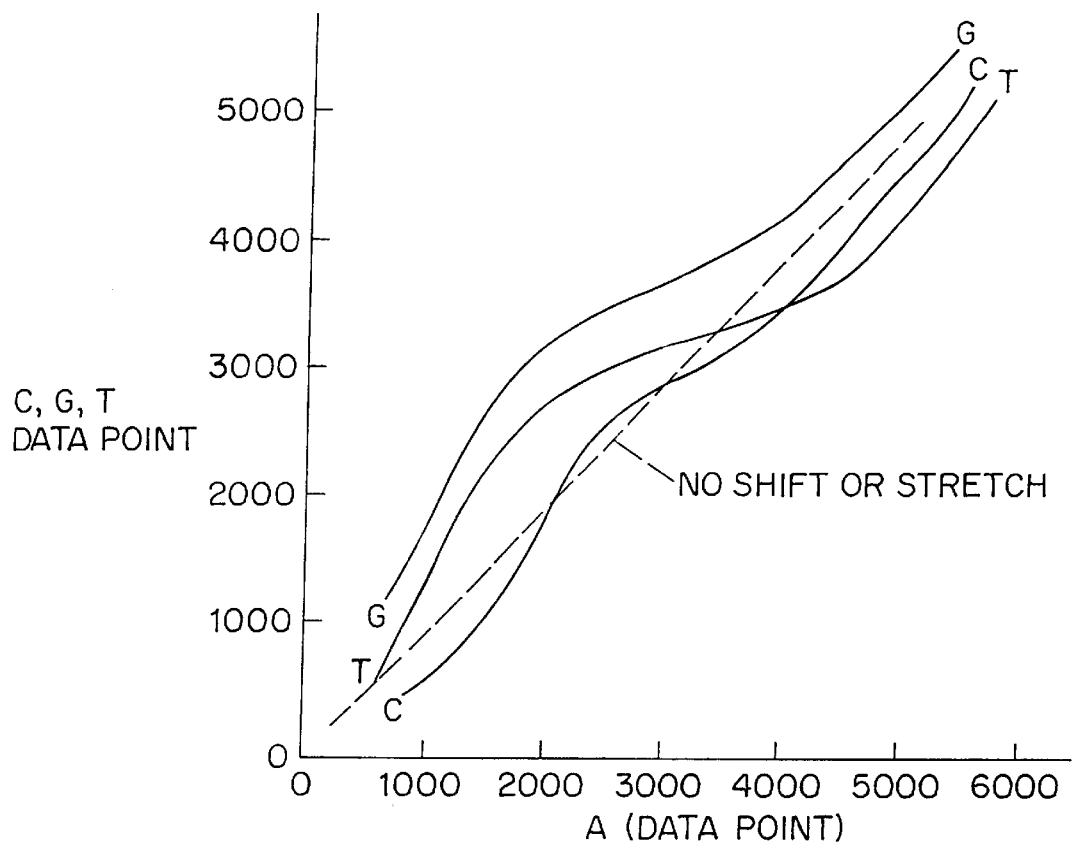
FIGS. 7A and 7B shows exemplary warp functions for data points in the C, G and T traces relative to the A trace.
Figure 7B:
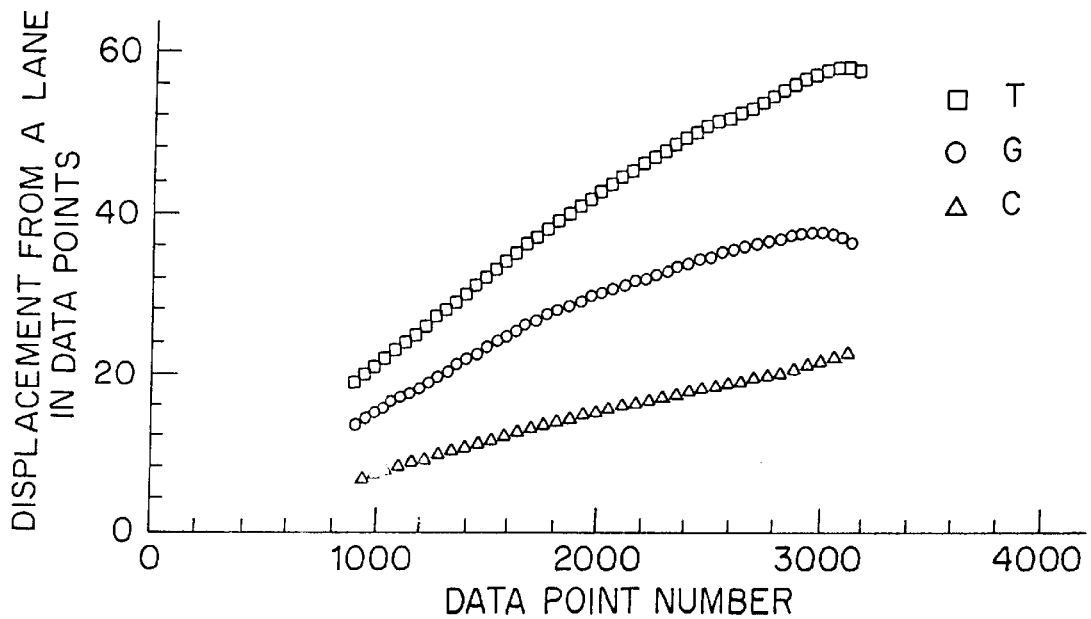

As a general matter, warp functions are generated in this way for each data trace. Thus, if the coefficients are determined with reference to a fixed standard, four different warp functions reflecting the varying coefficients needed to align the four data traces are generated. In practice, however, it will be understood that the warp functions may be determined relative to one of the four data traces. In this case, the coefficients for the one fixed data trace will all be one. In the context of this application, the phrase "generating a warp function for each normalized data trace" encompasses both of these embodiments. The warp function may be represented by a plot of alignment of data points of the three warped traces, e.g., C, G and T against A as shown in FIG. 7A or as a plot of displacement versus data point as shown in FIG. 7B.

Each warp function is applied to its respective raw or conditioned data trace to adjust the alignment of the data trace and generate a "warped data trace." The four warped data traces are then combined in alignment to produce an aligned data set.

An additional peak spacing warp function may be generated and applied to adjust for variations in peak spacing as part of creating the warped data traces. The peak spacing warp function, and also the base separation function useable as a standard trace, are generated by testing postulated peak separation values in successive windows of the data trace and minimizing a peak separation cost function for each window. A suitable cost function is $$\text{COS} T = \sum d^2$$

where d is the distance between each actual peak and a hypothetical peak located at the position fixed by the postulated peak separation value.

Presentation of the aligned data set may be done internally within a computer for use with base-calling functions, or it may involve display of the aligned data set on a video monitor. Either way, the presentation allows further use to be made of the modified output signals, for base-calling and other purposes. For example, the video display of aligned data may be useful to permit an operator to make manual adjustments, and to observe inaccuracies in base-calling.

Base-calling on the aligned data set may be performed in a variety of ways, including those base-calling techniques described in Tibbetts and Bowling (U.S. Pat. No. 5,365,455) and Dam et al (U.S. Pat. No. 5,119,316). A preferred approach to base-calling of the aligned data set is as follows.

Peaks in each warped data trace making up the aligned data set are identified in the same manner in which peak detection was performed prior to normalization of the data traces. A minimum peak height from the base-line may be selected by the operator to avoid spurious results. Identified peaks are then used for base-calling.

Occasionally, peaks may represent a plurality of bands. It is necessary to determine which peaks these are, and how many bands they represent. An excellent method to employ is gaussian deconvolution whereby a peak is deconvolved into one or more standard gaussian peaks representing singleton peaks. It is found that peaks generated from DNA sequencing reactions using T7 polymerase (Pharmacia, Sweden) and Thermo Sequenase™ (Amersham Life Sciences) generate the most consistent gaussian peaks.

Figure 8:
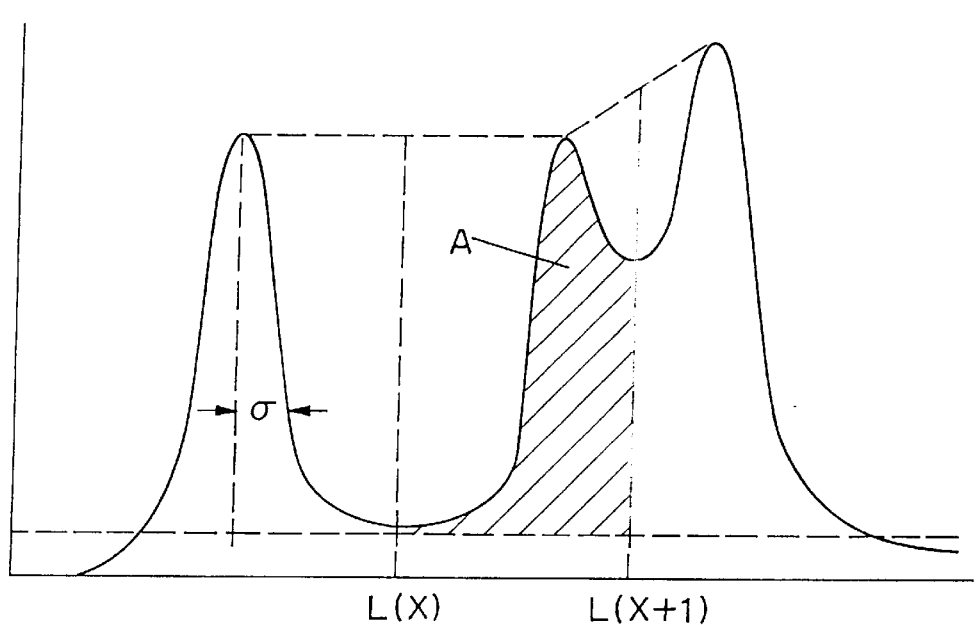
FIG. 8 illustrates a method for determining a standard gaussian peak width.

The standard gaussian peak is determined as shown in FIG. 8. Peaks are located in a conditioned data trace from one channel. A line is drawn between peak points. The point on the line halfway between peaks is joined to the data trace by a line L perpendicular to the baseline. The area under the curve A and between the two perpendicular lines (L(x), L(x+1)) is determined. Height (h) is measured from the baseline to the peak. h and A are used to calculate sigma ($\sigma$) according to the equation:

$$\sigma = \frac{A}{h\sqrt{\pi}}$$

where $\sigma$ represents the distance on the x-axis between the peak and the point at which the value of the gaussian function $$y = e^{-(x/\sigma)^2}$$

equals 1/e.

Figure 9:
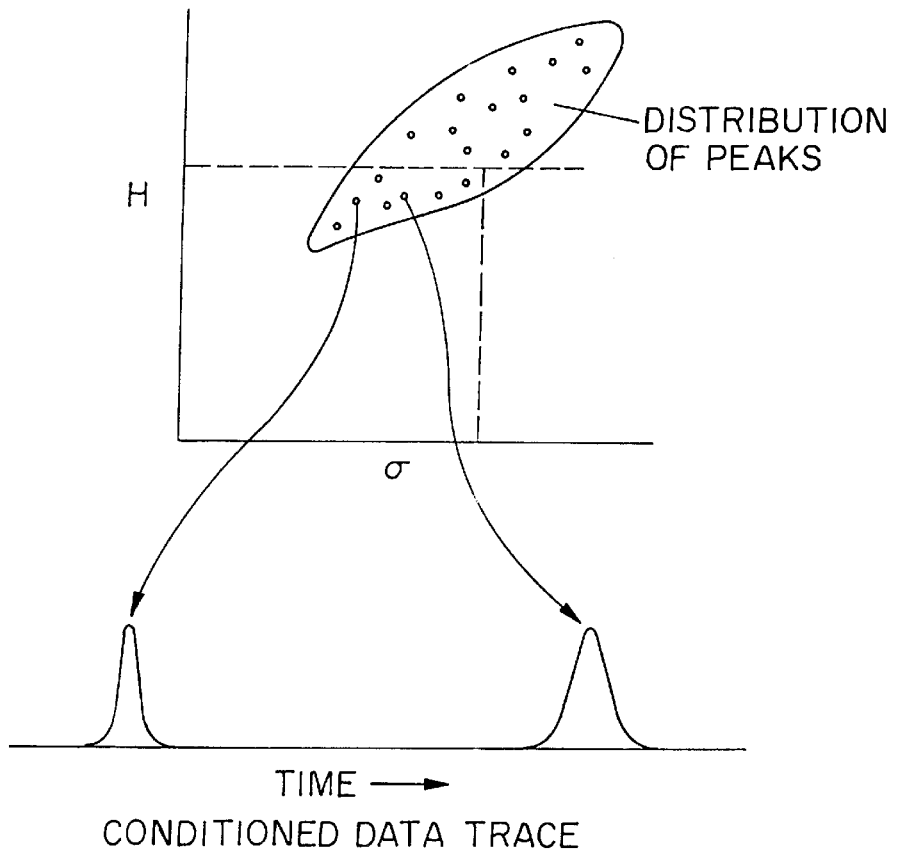
FIG. 9 shows an example of the classification of singletons using the features of peaks in the detected signal.

For each detected peak, $\sigma$ is determined. For those peaks where the length of both L(x) and L(x+1) are greater than ½ h, a linear regression is performed on the value of $\sigma$. Statistically, at most about 25% of peaks are expected to represent doubletons, triples or greater, so using the linear regression to correct for a width trend over each window, the narrowest 50% of the peaks are selected for use in constructing a piecewise cubic "singleton width discriminant function" that specifies the width of a singleton at each location in the data array. All peaks in the window that are narrower or equal to this function are deemed to be singletons to a first approximation. This approximation may be further refined using constraints such as peak area, etc. (FIG. 9) In this way, a standard or model singleton gaussian peak height and width at any point on the data trace may be defined.

The characteristics of the standard gaussian peak(s) and the positions of the singletons found via the discriminant function in conjunction with the base separation function are then used to classify all the peaks in the aligned data traces. The features (e.g., height, width and/or area) of the standard peak are compared to the features of a detected signal peak to determine the number of bases represented.

For example, if the standard spacing indicated by the base separation function is consistent with there being three peaks in a region between a pair of singletons and that region is occupied by a large peak, the characteristics of the standard gaussian peak (area, height etc.) are used to determine whether two, three or four peaks are most likely to be the number of base pairs represented by the large peak. Thus, for example, the difference between the area of the large peak and the area of the standard gaussian peak can be evaluated. If the area of the large peak is approximately three times the area of the standard peak, then the large peak is treated as representing three bases. Similarly, if the area is closer to four times the area of the standard peak, the large peak is treated as representing four bases. A similar, although less sensitive analysis can be performed based on the height of the peaks. The preferred analysis takes multiple peak features into account.

The primer peak may be eliminated or ignored as described for preparing the normalized signal output, so as not to interfere with base-calling.

Another method of identifying and eliminating the primer peak uses a peak counting method. The data stream is divided into windows of a certain number of data points. The peaks in each window are counted. When a primer peak is in the window, a window that normally would include 10 peaks, may have only 2 peaks. This window is eliminated from consideration, and other windows are used for alignment and base-calling.

Once the individual peaks are identified and the multiple peak curves are divided into individual gaussian peaks, the data may be base-called. Each peak is identified with one channel, representing a single base. Peaks are therefore assigned to specific bases, in sequential order, until the full sequence is identified.

Figure 10:
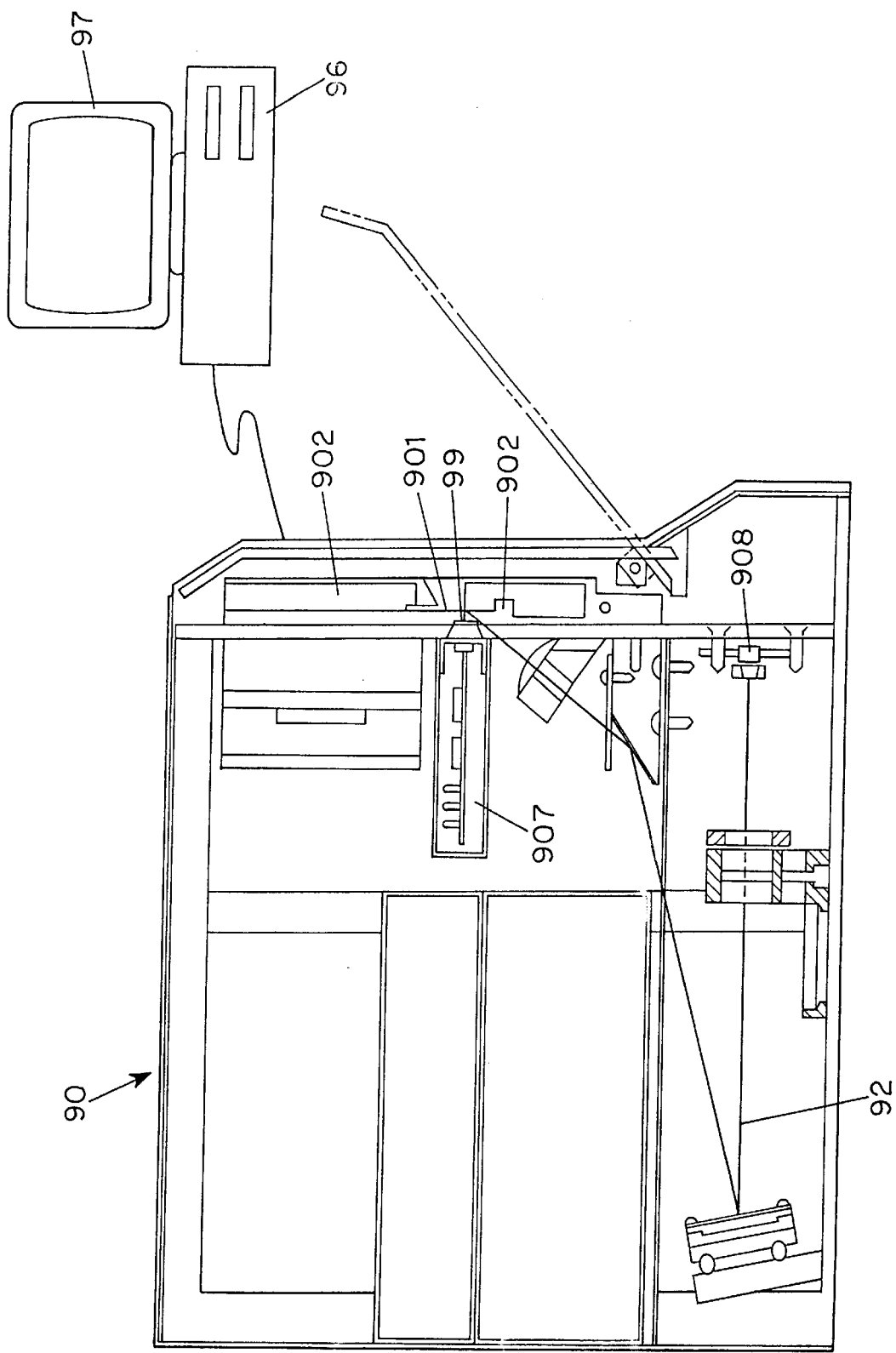
FIG. 10 shows an apparatus in accordance with the invention.

The method of the invention is advantageously practiced using a dedicated apparatus for determining nucleic acid sequences. As depicted in FIG. 10, such an apparatus comprises a sequencer 90 having an electrophoresis gel holder 901 disposed between electrodes 902 which are used to apply an electric field to a gel placed in the holder to cause oligonucleotide fragments to migrate within the gel; a detection system comprising a source 908 for an interrogating beam 92 and a detector 907 for detecting the passage of oligonucleotide fragments through a detection zone, for example by monitoring emitted light 99; and a data processing system 96 operatively connected to the detector 95 for receiving raw data traces for each of the four chain termination product mixtures for a sample. Suitable gel holders, electrodes and detection systems are disclosed in U.S. patent application Ser. No. 08/353,932, PCT Patent Application No. PCT/US95/15951, and U.S. patent application Ser. No. U.S. patent application Ser. No. 08/387,272, all of which are incorporated herein by reference, although it will be understood that the particular configuration of the electrophoresis and detection system is not critical to the present invention.

The data processing system is suitably a personal or mini-computer which has stored therein a programmed instruction set effective to identify peaks in each of the four data traces;

normalize the height of said peaks in each of said data traces to a common value to generate four normalized data traces;

combine the four normalized data traces in an initial alignment;

determine coefficients of shift and stretch for selected data points within each normalized data trace, said coefficients optimizing a cost function which reflects the extent of overlap of peaks in combined normalized data traces to which the coefficients have been applied, said cost function being optimized when the extent of overlap is at a minimum;

generate a warp function for each normalized data trace from the coefficients of shift and stretch determined for the selected data points;

apply each warp functions to the respective data trace or the normalized data trace to produce four warped data traces; and align the four warped data traces to form an aligned data set. The data processing system may be connected to a video display 97 for displaying the aligned data set.

In a preferred embodiment of the invention, the apparatus of the invention reports confidence levels to the system operator for some or all of the bases identified in the sequence. The confidence level advantageously reflects both (1) the arithmetic agreement between the signal and the model, and (2) other features of the data signal (for example expanded peak width) which may indicate reasons that the confidence level should be lower than the apparent level based on arithmetic agreements. This confidence level can be reported for all peaks, or it can be reported only for those peaks for which the confidence level falls below a selected threshold value. Peaks may also be flagged during the reporting process to report ambiguities in the identification of the number of bases represented by a multiple peak feature.

I claim:

1. A method for aligning data traces from four channels of an automated electrophoresis detection apparatus, each channel detecting the products of one of four chain-termination DNA sequencing reactions, whereby said four channels together provide information concerning the position of all four bases within a nucleic acid polymer being analyzed, comprising the steps of:

(a) identifying peaks in each of the four data traces;
   (b) normalizing the height of said peaks in each of said data traces to a common value to generate four normalized data traces;
   (c) combining the four normalized data traces in an initial alignment;
   (d) determining coefficients of shift and stretch for selected data points within each normalized data trace, said coefficients optimizing a cost function which reflects the extent of overlap of peaks in the combined normalized data traces to which the coefficients have been applied, said cost function being optimized when the extent of overlap is at a minimum;
   (e) generating a warp function for each normalized data trace from the coefficients of shift and stretch determined for the selected data points;
   (f) applying each warp functions to the respective data trace to produce four warped data traces; and
   (g) assembling the four warped data traces to form an aligned data set.

2. The method of claim 1, further comprising the step of displaying the aligned data set on a video display.

3. The method of claim 1, wherein the cost function determines the area of a region above the combined normalized data traces and below the common value, and wherein the cost function is optimized when this area is at a minimum.

4. The method of claim 3, further comprising the step of displaying the aligned data set on a video display.

5. The method of claim 1, wherein the cost function determines the area of a region below the combined normalized data traces, and wherein the cost function is optimized when this area is at a maximum.

6. The method of claim 1, wherein the cost function determines the area of a first region above the combined normalized data traces and the area of a second region, said second region being below the highest-edge of the combined normalized data traces and above the second highest edge of the combined data traces, wherein the cost function is optimized when the first area is minimized and the second area is maximized.

7. The method of claim 1, wherein the coefficients of shift and stretch for selected data points within each normalized data trace that yield the optimum value of the cost function are determined using a process of simulated annealing.

8. The method of claim 7, further comprising the step of displaying the aligned data set on a video display.

9. The method of claim 7, wherein the cost function determines the area of a region above the combined normalized data traces and below the common value, and wherein the cost function is optimized when this area is at a minimum.

10. The method of claim 7, further comprising the step of displaying the aligned data set on a video display.

11. The method of claim 7, wherein the cost function determines the area of a region below the combined normalized data traces, and wherein the cost function is optimized when this area is at a maximum.

12. The method of claim 7, wherein the cost function determines the area of a first region above the combined normalized data traces and the area of a second region, said second region being below the highest-edge of the combined normalized data traces and above the second highest edge of the combined data traces, wherein the cost function is optimized when the first area is minimized and the second area is maximized.

13. The method of claim 7, further comprising the step of conditioning the data traces prior to identification of the peaks in the data traces.

14. A method for determining the sequence of a nucleic acid polymer comprising the steps of:

(a) obtaining data traces from four channels of an automated electrophoresis detection apparatus, each channel detecting the products of one of four chain-termination DNA sequencing reactions, whereby said four channels together provide information concerning the position of all four bases within a nucleic acid polymer being analyzed;
   (b) aligning the data traces by a process comprising the steps of:
      identifying peaks in each of the four data traces;
      normalizing the height of said peaks in each of said data traces to a common value to generate four normalized data traces;
      combining the four normalized data traces in an initial alignment;
      determining coefficients of shift and stretch for selected data points within each normalized data trace, said coefficients optimizing a cost function which reflects the extent of overlap of peaks in combined normalized data traces to which the coefficients have been applied, said cost function being optimized when the extent of overlap is at a minimum;
      generating a warp function for each normalized data trace from the coefficients of shift and stretch determined for the selected data points;
      applying each warp function to the respective data trace to produce four warped data traces; and
      assembling the four warped data traces to form an aligned data set; and
   (c) evaluating the aligned data set to determine the sequence of bases within the nucleic acid polymer.

15. The method of claim 14, wherein the cost function determines the area of a region above the combined normalized data traces and below the common value, and wherein the cost function is optimized when this area is at a minimum.

16. The method of claim 15, wherein the cost function determines the area of a region below the combined normalized data traces, and wherein the cost function is optimized when this area is at a maximum.

17. The method of claim 15, wherein the cost function determines the area of a first region above the combined normalized data traces and the area of a second region, said second region being below the highest-edge of the combined normalized data traces and above the second highest edge of the combined data traces, wherein the cost function is optimized when the first area is minimized and the second area is maximized.

18. The method of claim 14, wherein the coefficients of shift and stretch for selected data points within each normalized data trace that yield the optimum value of the cost function are determined using a process of simulated annealing.

19. The method of claim 18, wherein the cost function determines the area of a region above the combined normalized data traces and below the common value, and wherein the cost function is optimized when this area is at a minimum.

20. The method of claim 18, wherein the cost function determines the area of a region below the combined normalized data traces, and wherein the cost function is optimized when this area is at a maximum.

21. The method of claim 18, further comprising the step of conditioning the data traces prior to identification of the peaks in the data traces.

22. The method of claim 18, wherein the cost function determines the area of a first region above the combined normalized data traces and the area of a second region, said second region being below the highest-edge of the combined normalized data traces and above the second highest edge of the combined data traces, wherein the cost function is optimized when the first area is minimized and the second area is maximized.

23. The method according to claim 14, further comprising the steps of determining standard gaussian peak shapes for data points along the aligned data set;

assigning peaks in the aligned data set as singleton peaks or multiple peaks by comparison of the peaks in the aligned data set to the standard gaussian peak characteristics; and determining how many standard gaussian peaks are contained within each multiple peak, wherein each multiple peak is treated as that number of singleton peaks for purposes of base-calling.

24. The method according to claim 14, further comprising the step of reporting confidence levels for at least a portion of the called base peaks.

25. The method according to claim 24, wherein the confidence level reflects the arithmetic agreement between the peak in the data trace and a standard peak, and those features of the peak which might justify assignment of a lower confidence level.

26. An apparatus for determining the sequence of a nucleic acid polymer comprising:

(a) an electrophoresis gel holder;

(b) first and second electrodes disposed to apply an electric field to the electrophoresis gel disposed within the electrophoresis gel holder to cause oligonucleotide fragments loaded on the electrophoresis gel to migrate within the electrophoresis gel;

(c) a detection system comprising an interrogating beam and a detector for detecting the passage of oligonucleotide fragments through a detection zone; and (d) a data processing system operatively connected to the detector for receiving four data traces, one for each of four chain termination product mixtures for the nucleic acid polymer, wherein the data processing system has stored therein a programmed instruction set effective to identify peaks in each of the four data traces;

normalize the height of said peaks in each of said data traces to a common value to generate four normalized data traces;

combine the four normalized data traces in an initial alignment;

determine coefficients of shift and stretch for selected data points within each normalized data trace, said coefficients optimizing a cost function which reflects the extent of overlap of peaks in combined normalized data traces to which the coefficients have been applied, said cost function being optimized when the extent of overlap is at a minimum;

generate a warp function for each normalized data trace from the coefficients of shift and stretch determined for the selected data points;

apply each warp functions to the respective data trace to produce four warped data traces; and assemble the four warped data traces to form an aligned data set.

27. The apparatus according to claim 26, further comprising a video display for displaying the aligned data set.

* * * * *

UNITED STATES PATENT AND TRADEMARK OFFICE
CERTIFICATE OF CORRECTION

PATENT NO : 5,916,747
DATED : June 29, 1999
INVENTOR(S) : Gilchrist, Rodney D. and Chi, Vrijmoed It is certified that error appears in the above-identified patent and that said Letters Patent are hereby corrected as shown below:

Cover page, Section [54], delete "BASED-CALLING" and insert --BASE-CALLING--

Cover page, Section [56], Column 2, line 17, delete "Techqniues" and insert --Techniques--

Cover page, Section [57], line 14, delete "function" and insert --functions--

Column 1, line 3, delete "BASED-CALLING" and insert --BASE-CALLING--

Column 1, line 27, delete "A, C, C," and insert --A, C, G,--

Column 2, line 16, delete "an" and insert --a--

Column 2, line 50, delete "fsthe" and insert --the--

Column 5, line 54, delete "embodiments" and insert --embodiment--

Column 7, line 4, delete "coefficient" and insert --coefficients--

Column 7, line 40, delete "increase" and insert --increases--

Column 10, lines 46 and 47, delete "U.S. patent application Ser. No.", first occurrence Column 11, line 4, delete "functions" and insert --function--

UNITED STATES PATENT AND TRADEMARK OFFICE
CERTIFICATE OF CORRECTION

PATENT NO : 5,916,747

DATED : June 29, 1999

INVENTOR(S) : Gilchrist, Rodney D. and Chi, Vrijmoed

It is certified that error appears in the above-identified patent and that said Letters Patent are hereby corrected as shown below:

Column 11, line 49, delete "functions" and insert --function--

Column 14, line 46, delete "functions" and insert --function--

Signed and Sealed this

Fourteenth Day of December, 1999

Attest:

Q. TODD DICKINSON

Attesting Officer

Acting Commissioner of Patents and Trademarks